United States Patent [19]

Rechsteiner

[11] Patent Number: 4,612,813
[45] Date of Patent: Sep. 23, 1986

[54] APPARATUS FOR AN ULTRASONIC MEASURING OF A FLOW QUANTITY AND A METHOD OF ULTRASONICALLY MEASURING A FLOW QUANTITY

[75] Inventor: Alfred Rechsteiner, Uster, Switzerland

[73] Assignee: Doltron AG, Uster, Switzerland

[21] Appl. No.: 469,644

[22] Filed: Feb. 25, 1983

[30] Foreign Application Priority Data

Feb. 26, 1982 [CH] Switzerland ................. 1216/82

[51] Int. Cl.$^4$ .............................................. G01F 1/66
[52] U.S. Cl. ................................................. 73/861.25
[58] Field of Search ......................... 604/4; 73/861.25

[56] References Cited

U.S. PATENT DOCUMENTS

| 3,741,014 | 6/1973 | Tamura | 73/861.25 |
| 4,048,853 | 9/1977 | Smith et al. | 73/861.25 |
| 4,147,059 | 4/1979 | Fathauer | 73/861.25 |
| 4,333,352 | 6/1982 | Connery et al. | 73/861.18 |

Primary Examiner—Charles A. Ruehl

Attorney, Agent, or Firm—Charles E. Brown; Charles A. Brown

[57] ABSTRACT

An apparatus for and a method of extracting physiological liquids and adding of a coagulation preventing element thereto such to control the added quantity of the coagulation preventing agent in accordance with the quantity of flow of the physiological liquid such that at all times a set ratio between the flow quantity of the physiological liquid and of the coagulation preventing agent is maintained. This allows an improvement of the yield and of the durability of the physiological liquid. The apparatus comprises an emitter element, a transducer including two oscillators which are to be applied onto a plastic hose flowed through by the physiological liquid, comprises further a demodulating circuit which generates a signal which is proportional to the velocity of speed within the plastic hose, comprises further a converter which generates a DC-signal which is proportional to the flow quantity. The measuring proceeds without contact and without any influence onto the medium being measured.

17 Claims, 6 Drawing Figures

APPARATUS FOR AN ULTRASONIC MEASURING OF A FLOW QUANTITY AND A METHOD OF ULTRASONICALLY MEASURING A FLOW QUANTITY

BACKGROUND OF THE INVENTION

1. Field of the Invention

The present invention relates to an improved apparatus for an ultrasonic measuring of the quantity of a flow within a plastic hose by means of an emitter and a transducer which is connected to the emitter and generates a signal which is proportional to the velocity or the speed of the flow within the plastic hose and having an analyzing means which generates a signal which is proportional to the quantity of flow. The invention relates further to a method of extracting physiological liquids and adding thereto a proportional amount of a liquid coagulation preventing agent by means of an instrument system applied to a donator and a peristaltic pump for introducing the coagulation preventing agent.

2. Description of the Prior Art

The present procedure for extracting blood from donators is to lead the blood donated into a bag or a bottle, in which bag or bottle, respectively, an agent for the prevention of a coagulation as well as for conserving the blood has been previously added.

However, according to this well-known method the ideal ratio of mixture of the two components is reached not earlier than after the termination of the extraction of blood such that during the beginning of the procedure a surplus of the coagulation preventing agent is present which will destroy partly or completely important components and cells of the blood. Accordingly, the quality and durability of a blood conserve is reduced or restricted, respectively.

SUMMARY OF THE INVENTION

Hence, it is a general object of the present invention to provide an improved apparatus and a method for an ultrasonic measuring of the quantity of flow of blood extracted from a donator such to allow at all times during the donating procedure a correctly measured quantity of a coagulation preventing agent.

A further object is to provide an improved apparatus for an ultrasonic measuring of the quantity of a flow within a plastic hose without direct contact of the transducer means with the medium to be measured, which apparatus is provided with two oscillator elements in its transducer means, which oscillator elements are intended to contact the outer surface of the hose and is provided further with a demodulator means in the transducer means having at least one selectively controlled amplifier and a demodulator designed such that the ratio of the intelligence signal/disturbance signal amounts to at least about 2:1, and having further a converter means including at least one control amplifier, a demodulator and a calibrating amplifier such to generate a DC-signal, which is proportional to the quantity of flow.

A further object of the invention is to provide an apparatus and a method of extracting physiological liquids and adding a proportional amount of liquid coagulation preventing agents, according to which the measuring device does not contact the donated liquid and plastic hoses can be used which are readily available on the market.

A further object is to provide an apparatus in which the transducer means includes a body having an elongated recess intended to receive a section of the hose and includes further a cover intended to lock the hose section in the elongated recess. The advantage of such construction is that the hose section located in the recess and accordingly at the transducer has a predetermined cross-sectional area allowing a safe transducing and measuring, respectively, of the flow quantity.

A further object is to provide oscillator elements which consist of piezoelectric crystals and being embedded in the body at a mutual distance from each other such that at least a surface area of the oscillator elements form together with the surface of the recess a continuous surface for supporting the hose.

Yet a further object is to provide an apparatus in which the oscillating elements extend parallel to the longitudinal axis of the recess and such that the surface areas facing the recess define an angle of at least about 90°. The advantage thereof is that the area of measurement is located substantially in the center of the hose and that a larger portion of the signal penetrated therein will not be reflected such that the ratio intelligence signal/disturbance signal is improved.

A further object is to provide the emitter means with a temperature compensated control circuit generating an output signal with a frequency of about 9.5 MHz and to design the calibrating amplifier as an adjustable amplifier such to transform the signal which is proportional to the velocity of flow into a signal which is proportional to the quantity of flow.

Yet a further object of the invention is to provide a method of extracting physiological liquids and adding a proportional amount of a liquid coagulation preventing agent by means of an instrument system to be applied on a donator, which system includes a liquid receiving bag and a plastic hose intended to be applied on the one hand to the donator and on the other hand to the liquid receiving bag and including a peristaltic pumping means for the supply of the coagulation preventing agent, which method comprises the steps of ultrasonically measuring the quantity of flow within the plastic hose by means of an apparatus including an emitter means emitting an output signal in the frequency range of about 2 to 5 MHz, including a transducer means connected to the emitter means and emitting a signal which is proportional to the velocity of flow within the hose, including an analyzing means or a signal shape analizer having a signal shaper for generating a signal proportional to the quantity of flow within the hose; of providing two oscillator elements in the transducer means and applying the oscillator elements onto the outer surface of the hose, providing a demodulator means in the transducer means having at least one selectively controlled amplifier and demodulator designed such that the ratio intelligence signal/disturbance signal amounts to at least about 2:1, having further a converter means including at least one control amplifier, a demodulator and a calibrating amplifier generating a DC-signal being proportional to the quantity of flow; of providing a second bag containing the coagulation preventing agent, a second plastic hose and a connector and connecting therewith the first plastic hose to the second plastic hose; of placing the transducer means onto the first plastic hose such to measure the quantity of the donated physiological liquid; of placing the peristaltic pump onto the second plastic hose and operationally connecting the pump to the analyzing means such to transport a quantity of the coagulation preventing agent into the first plastic hose which is proportional to the quantity of the donated liquid.

The advantages derived from such method are substantially that the ratio in the mixture consisting of physiological liquid and coagulation preventing agent can be exactly maintained during the period of donating at a predetermined level such that the quality and durability of the donated liquid may be improved.

This is specifically advantageous regarding the yield when the donated blood is dissected for a precise blood component therapy.

BRIEF DESCRIPTION OF THE DRAWINGS

The present invention will be more fully understood by reference to the following detailed description thereof, when read in conjunction with the attached drawings, and wherein.

DETAILED DESCRIPTION OF THE PREFERRED EMBODIMENTS

Figure 1:
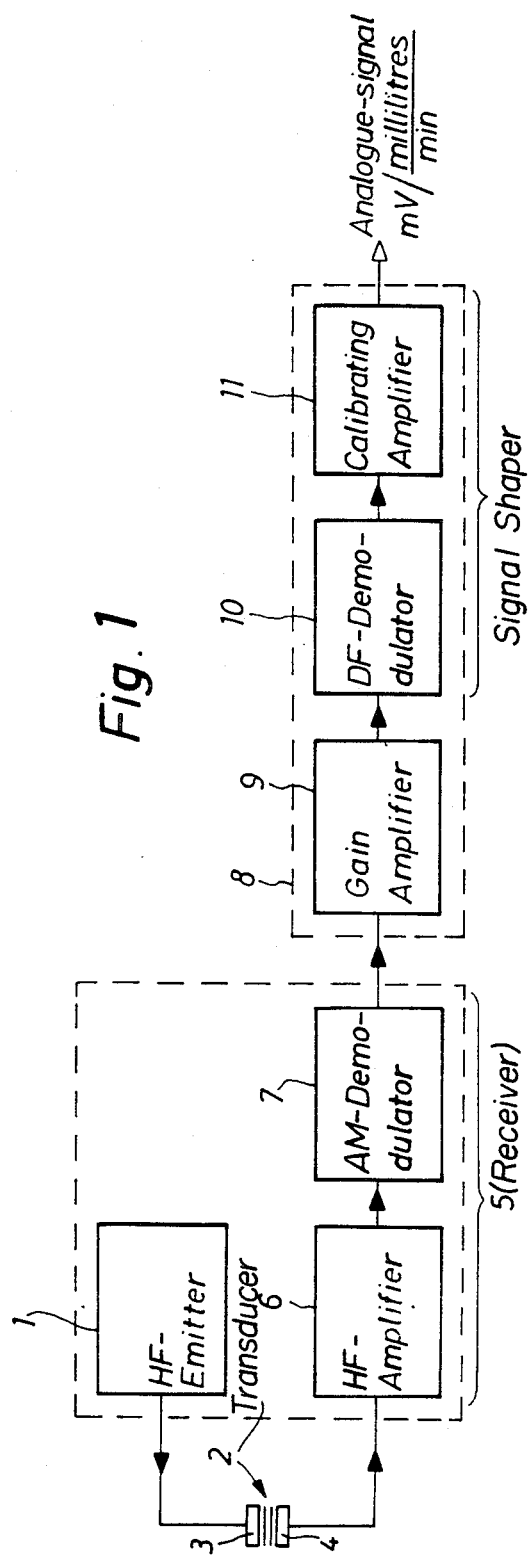
FIG. 1 is a block diagram of a preferred embodiment of the apparatus in accordance with the invention.
Figure 2:
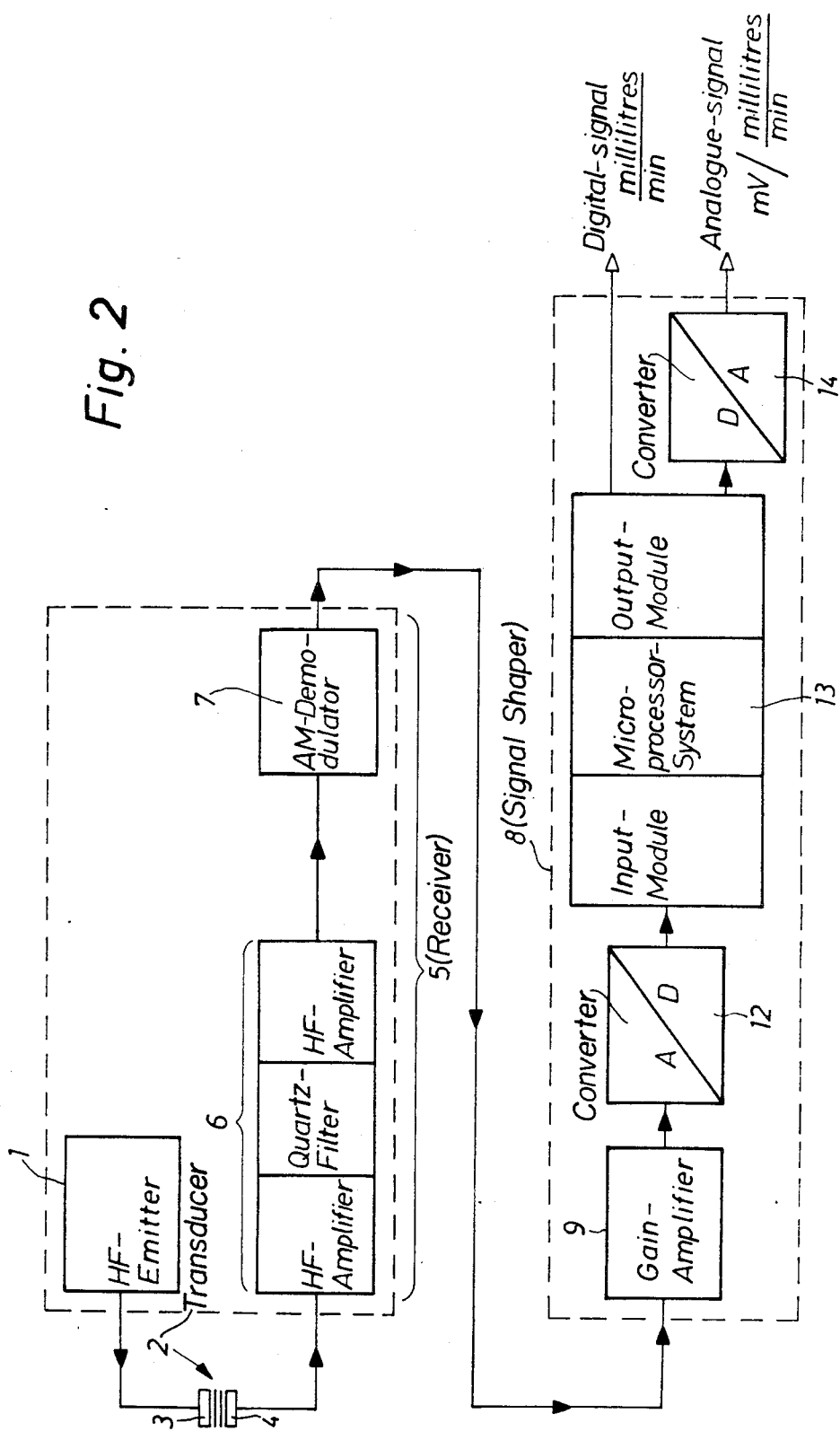
FIG. 2 is a block diagram of a further preferred embodiment of the inventive apparatus.

In accordance with FIGS. 1 and 2 the apparatus comprises basically an emitter element 1, a transducer 2 and an analyzing system. The transducer 2 comprises two oscillators 3 and 4, which are electrically coupled to the emitter element 1 and analyzing system, respectively, and which are applicable onto a plastic hose.

The analyzing system of FIG. 1 comprises a demodulator circuit 5 having a selectively controlled amplifier 6 and a demodulator 7 connected in series which acts as a receiver, and a converter circuit 8 including a gain amplifier 9, a demodulator 10 and a calibrating amplifier 11 which acts as a signal shaper.

Figure 5:
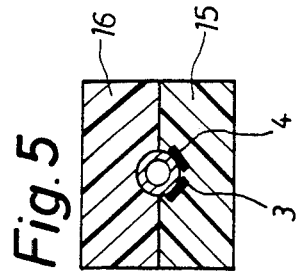
FIG. 5 is a section through the transducer shown in FIG. 4 including its cover.
Figure 4:
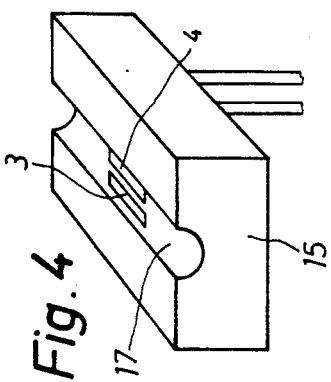
FIGS. 3 and 4 are special views of embodiments of a section of a transducer without its cover.
Figure 3:
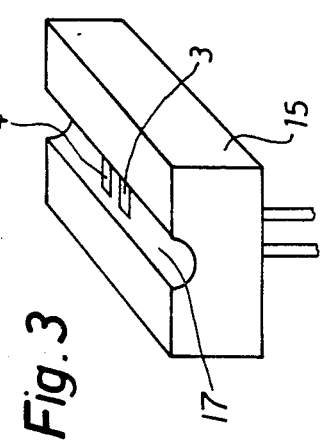

The transducer 2—see FIGS. 3, 4, 5—comprises a transducer body 15 having an elongated recess 17 intended to receive the plastic hose and a cover 16 which is mainly used to arrest or lock, respectively, the hose inside of the transducer body 15. Due to mentioned arresting the oscillator elements 3, 4 located in the recess 17 at a mutual distance from each other will be pressed against the outer surface of the hose located in mentioned elongated recess 17. In order to achieve an excellent transmission of the oscillations the contact between the oscillating elements 3, 4 and the outer surface of the hose must be as far as possible without any air gap.

In the embodiment according to FIG. 3 the oscillating elements 3, 4 extend laterally relative to the longitudinal axis of the recess 17.

In accordance with the embodiment shown in FIGS. 4, 5 these oscillator elements 3, 4 extend parallel to the longitudinal axis of the recess 17. The oscillating elements 3, 4 define together an angle such that a certain focusing is formed such, that the measuring proper is made in the center of the hose, at which location the flow speed of the liquid flowing therethrough is the largest. This improves the ratio intelligence signal/disturbance signal.

The emitter element 1 which is arranged and temperature compensated such that it has an equal temperature operation relative to the other elements of the demodulator circuit emits an output signal of 9.5 MHz, which output signal is led to one oscillator element 3 of the transducer.

The oscillator 3 consisting of piezoelectrical crystal material will oscillate mechanically by the signal emitted from the emitter element 1. This oscillation will be transmitted via the wall of the hose onto the medium flowing in the hose. This oscillation is reflected at the hose, at the transducer including cover 15, 16 as well as at particles in the flowing medium. The oscillation reflected by the particles of the flowing medium has a shift of frequency which is proportional to the flow velocity of the flowing medium (Doppler-effect). This technique is known but not yet practicable for measuring blood flow in a closed hose system.

The second oscillator element 4 of the transducer will be excited by the reflected oscillation and emits an electrical output signal. The amplifier 6 arranged after the oscillating element 4 prepares the HF-signal such that it can be demodulated by the following demodulator 7. The HF-amplifier 6 as well as the demodulator 7 are designed such that an as high as possible suppressing of those frequencies which do not contain information is carried out for the known receiving frequencies. The low frequency-signal generated thereby and having a frequency which is proportional to the velocity of the flow is led thereafter to the converter circuit 8 in which the low frequency-signal is shaped.

A gain amplifier 9 comprised in the converter circuit 8 achieves a further improvement of the low frequency-signal, specifically regarding the intelligence signal/disturbance signal-relation, whereafter this signal is transformed in a following demodulator 10 into a DC-voltage. This voltage is now proportional to the velocity of the flowing medium. Because the calibrating amplifier 11 operates adjustably, the signal can be emitted linearly and in proportion to the quantity of flow.

The system of FIG. 2 is designed primarily in accordance with the known configuration of FIG. 1, differs however regarding the arrangement inside its demodulator circuit 5, in that the HF-amplifier 6 is provided with quartz filters allowing an improvement of the selectivity.

The converter circuit 8 performs the shaping of the low frequency-signal but is designed substantially different in that the low frequency-signal is transformed after the gain amplifier 9 by means of the analogue/digital converter 12 into a digital signal. In this form the signal may now be handled by a microprocessor system 13. Apart of the transforming of the signal units which are proportional to the velocity of flow into signal units which are proportional to the quantity of flow further evaluations and influences of the signals may be carried out. Examples are for instance: picking up of the threshold limit and maximal values, of changes, generation of linear and nonlinear output curves.

At the output side of the microprocessor system 13 the output signal is present in a digital form or after a further change in the digital/analogue-converter in form of a DC-signal.

Figure 6:
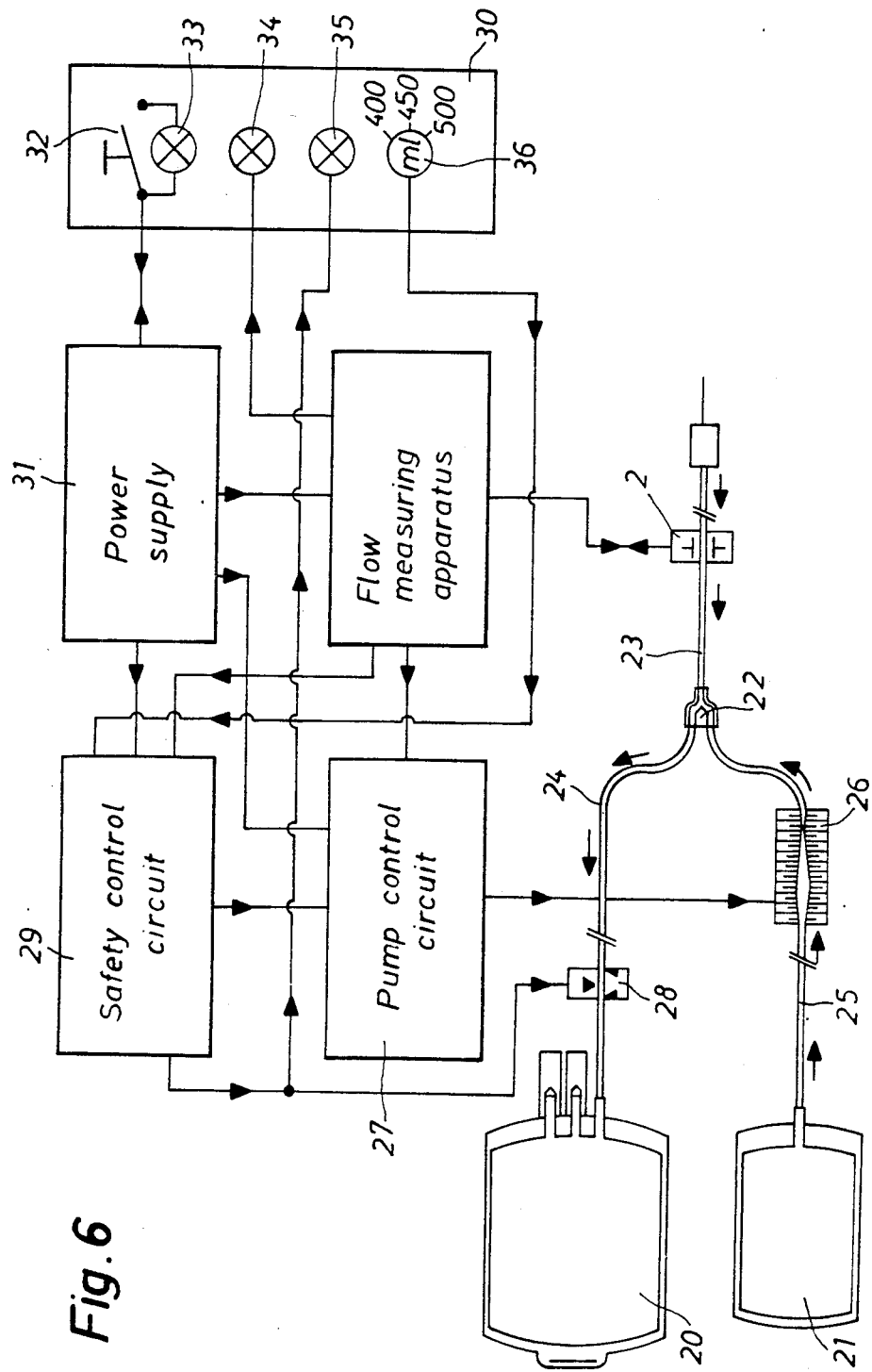
FIG. 6 is a schematic representation of a system for extracting a donated physiological liquid and mixing thereto a coagulation preventing agent and incorporating the inventive apparatus.

FIG. 6 discloses a block circuit showing a system for extracting blood and mixing a coagulation preventing agent thereto including the necessary instruments.

These instruments are basically a first bag 20 intended to receive the donated blood, a second bag 21 in which the coagulation preventing agent is stored and a hose arrangement which interconnects the donator and the first and second bags 20, 21. This hose arrangement comprises a connector 22 and three plastic hoses 23, 24, 25, which are coupled on the one hand to the connector 22 and on the other hand to the donator, to the first bag and to the second bag 20, 21, respectively.

The connector 22 comprises a Y-shaped flow channel and the stem of this flow channel is coupled to the plastic hose 23 leading to the donator and the legs of the Y being coupled to the plastic hoses 24, 25 leading to the first and second, respectively, bag.

Such as clearly shown in FIG. 6, the system allowing the embodiment of the method and comprising the above described flow measuring apparatus which is applied via transducer 2 to the plastic hose 23 leading to the donator such to allow a measuring of the donated quantity of blood comprises a peristaltic pump 26 and a pump control circuit 27 which is applied onto the plastic hose 25 leading to the second bag 21, through which the coagulation preventing element is introduced, further a shut-off element 28 including a safety control circuit 29, a display and control section 30 as well as a power supply section 31.

The design of the peristaltic pump 26 as such is generally known and, for instance, disclosed in the U.S. Pat. No. 4,302,164 and reference is made herewith thereto. The shut-off element 28 comprises two members which are movable towards each other (not specifically shown), which if operated press the plastic hose 24 together and accordingly interrupt the flow therethrough.

The display and control section 30 is provided with a switch 32 to switch the system on or off, is provided further with an indicator lamp 33 which indicates if the system is in operation, a further indicating lamp 34 for indicating that the blood is being donated, a lamp 35 to indicate that the donation has been interrupted or terminated and, furthermore, a selection switch 36 for adjusting the quantity of blood being extracted.

The power supply section 31 is connected to the flow measuring apparatus, to the pump control circuit 27 and to the safety control circuit 29 and supplies the power thereto.

The flow measuring apparatus is connected to the control circuit 27 and the safety circuit 29. The safety circuit 29 is in turn connected to the shut-off element 28 and to the pump control circuit 27.

When operating the blood extracting system, such is switched on and connected to the donator as is generally known. The peristaltic pump 26 is operated temporarily such to transport the coagulation preventing agent up to the connector 22. Thereafter the peristaltic pump 26 is switched off.

As soon as the blood begins to flow through the plastic hose, the flow measuring apparatus delivers the signal corresponding to the measured flow to the safety control circuit 29 allowing the determination of the total through flow quantity and to the pump control circuit 27 such to initiate again the operation of the peristaltic pump 28 and to control the pump in accordance with mentioned signal. Accordingly, the peristaltic pump 27 transports a quantity of the coagulation preventing agent which corresponds to a previously calculated ratio into the connector 22. Because the coagulation preventing agent is transported in the counterflow relative to the flow of the blood, an excellent mixing is achieved within the connector 22.

The safety control circuit 29 comprises threshold control circuits (not particularly shown), which after the quantity which has been preset by means of the selection switch 36 has been reached, operate the shut-off element 28 such that the extraction of blood is terminated and which in case that the actual through flow falls below the preset through flow initiate an acoustic signal indicating that the extraction of blood is not operating optimally.

While there are shown and described present preferred embodiments of the invention, it is to be distinctly understood that the invention is not limited thereto, but may be otherwise variously embodied and practiced within the scope of the following claims. Accordingly,

What is claimed is:

1. An apparatus for an ultrasonic measuring of the quantity of liquid flow within a plastic hose by means of emitter means emitting a predetermined high frequency output signal having a frequency in a range of 2 to 15 MHz, said apparatus having transducer means electrically connected to said emitter means and emitting a signal which is proportional to the flow velocity of the liquid and operatively associated to a section of said hose for transmitting said signal of said transducer means into the liquid flowing through said section of said hose and for receiving a signal backscattered by the liquid flowing through said section of said hose and having further a signal shape analyzer electrically connected to said transducer means generating an output signal which is proportional to the quantity of flow of said liquid flowing through said hose wherein said transducer means comprises two oscillator elements designed to make contact with the outer surface of said section of said hose; said transducer means further comprising a demodulator means having at least one selectively controlled amplifier connected to one of said oscillator elements and a demodulator connected to said amplifier; said amplifier and said demodulator providing an output signal comprising an intelligence signal provided by the liquid flowing through the hose and a disturbance signal provided by the hose and the ratio of the intelligence signal to the disturbance signal amounts to at least 2:1, and said analyzer having at least one control amplifier connected to said demodulator means, a further demodulator connected to said control amplifier and a calibrating amplifier connected to said further demodulator in order to generate a DC-signal which is proportional to the quantity of flow of the liquid flowing through said section of said hose.

2. The apparatus of claim 1, wherein said transducer means includes a body having an elongated recess intended to receive said hose section and includes further a cover intended to lock said hose section in said elongated recess.

3. The apparatus of claim 2, in which said oscillator elements are in the form of piezoelectric crystals and are embedded in said body at a mutual distance from each other such that at least a surface area of said oscillator elements forms together with the surface of said elongated recess a continuous supporting surface for said hose section.

4. The apparatus of claim 3, in which said oscillating elements extend laterally to the longitudinal axis of said elongated recess.

5. The apparatus of claim 3, in which said oscillating elements extend parallel to the longitudinal axis of said recess and the surface areas facing said recess define an angle of at least 90°.

6. The apparatus of claim 1, wherein said emitter means has a temperature compensated control circuit generating an output signal with a frequency of about 9.5 MHz.

7. The apparatus of claim 1, wherein said calibrating amplifier is an adjustable amplifier for transforming said signal which is proportional to the velocity of flow into a signal which is proportional to the quantity of flow.

8. The apparatus of claim 1, wherein said controlled amplifier of said demodulator means is provided with quartz filters for improving the selectivity of the output signal of said transducer.

9. An apparatus for an ultrasonic measuring of the quantity of blood flowing in a plastic hose from a donor, which apparatus comprises an emitter emitting a predetermined high frequency output signal having a frequency in a range of 2 to 15 MHz; a transducer including a two-piece housing into which said plastic hose is insertable and including two oscillator elements for transmitting a signal corresponding to said output signal of said emitter into the blood flowing through said plastic hose and for receiving a signal backscattered by the blood flowing through said plastic hose; which signal is proportional to the velocity of flow; and a signal shape analyzer having a receiver, a control amplifier and a signal shaper, which signal shape analyzer is connected to said transducer for generating an output signal which is proportional to the quantity of flow, wherein said emitter provides an output signal having a frequency of 9.5 MHz; said transducer including an opening fitted to the cross section of said plastic hose; said oscillator elements being disposed such that at least a surface area of said oscillator elements form together with the surface of said opening a continuous supporting surface of said hose; said receiver including a selectively controlled amplifier and a subsequently added demodulator, said amplifier and demodulator providing an output signal comprising an intelligence signal and a disturbance signal, the ratio of the intelligence signal to the disturbance signal amounts to at least 2:1, said signal shaper includes a calibrating means for transforming said output signal of said signal shaper which is proportional to the velocity of flow of the blood flowing through said hose to said output signal of the apparatus which is proportional to the quantity of flow of blood flowing through said hose.

10. The apparatus of claim 9, wherein said calibrating means is an adjustable amplifier.

11. The apparatus of claim 9, wherein said housing includes a body and a cover for determining said cross section of said opening such that the plastic hose inserted into said housing has a predetermined cross section in the region of said transducer and there is defined a recess in which the plastic hose is supported.

12. The apparatus of claim 11, in which said oscillating elements extend laterally to the longitudinal axis of said recess.

13. The apparatus of claim 11, in which said oscillating elements extend parallel to the longitudinal axis of said recess and the surface areas facing said recess define an angle of at least 90°.

14. The apparatus of claim 9, said emitter having a temperature compensated control circuit.

15. The apparatus of claim 9, wherein said controlled amplifier of said receiver is provided with quartz filters for improving the selectivity of said output signal of said receiver.

16. The apparatus of claim 9, wherein said signal shaper comprises a microprocessor system to which an analogue to digital converter is lined up.

17. The apparatus of claim 16, wherein at least one digital to analogue converter is subsequently added to said signal shaper.

* * * * *